United States Patent
Gradel et al.

(10) Patent No.: US 9,629,583 B2
(45) Date of Patent: Apr. 25, 2017

(54) DEVICE FOR MONITORING A MEDICAL PROSTHESIS AND THE HUMAN BODY

(75) Inventors: Thomas Gradel, Marignier (FR); Gérard Weil, Sainte Foy les Lyon (FR); Lionel Piffault, Montils (FR); Fabien Gaucher, Lyons (FR)

(73) Assignee: LAPE MEDICAL, Scionzier (FR)

( * ) Notice: Subject to any disclaimer, the term of this patent is extended or adjusted under 35 U.S.C. 154(b) by 626 days.

(21) Appl. No.: 14/003,293

(22) PCT Filed: Mar. 5, 2012

(86) PCT No.: PCT/IB2012/051030
§ 371 (c)(1),
(2), (4) Date: Sep. 5, 2013

(87) PCT Pub. No.: WO2012/120439
PCT Pub. Date: Sep. 13, 2012

(65) Prior Publication Data
US 2013/0338455 A1 Dec. 19, 2013

(30) Foreign Application Priority Data
Mar. 7, 2011 (FR) .................... 11 51857

(51) Int. Cl.
*A61B 5/00* (2006.01)
*A61F 2/30* (2006.01)
(Continued)

(52) U.S. Cl.
CPC .......... *A61B 5/4851* (2013.01); *A61B 5/0002* (2013.01); *A61B 5/0059* (2013.01); *A61B 5/01* (2013.01); *A61B 5/03* (2013.01); *A61B 5/11* (2013.01); *A61B 5/14539* (2013.01); *A61B 5/686* (2013.01); *A61B 5/6878* (2013.01); *A61B 5/7246* (2013.01); *A61F 2/30721* (2013.01); *A61F 2/4657* (2013.01); *A61B 17/56* (2013.01);
(Continued)

(58) Field of Classification Search
CPC ......... A61B 5/4851; A61B 5/076; A61B 5/11; A61B 5/6878; A61B 5/6867; A61F 2/4657
See application file for complete search history.

(56) References Cited

U.S. PATENT DOCUMENTS

| 6,706,005 B2 * | 3/2004 | Roy | A61B 5/4504 600/594 |
| 7,753,903 B1 * | 7/2010 | Burton | A61B 5/076 600/316 |

(Continued)

FOREIGN PATENT DOCUMENTS

| DE | 102008005180 A1 | 11/2008 |
| EP | 2106747 A1 | 10/2009 |

(Continued)

*Primary Examiner* — Eric Winakur
(74) *Attorney, Agent, or Firm* — William H. Eilberg (57) ABSTRACT

A device for monitoring a medical prosthesis and the human body includes a sensor for generating signals depending on surrounding stresses, a processor for processing the signals emitted by the sensor in order to convert the signals into data, a storage device for storing the data, a device for wireless transmission of the stored data, and a supply of electrical energy. The device is included in at least one casing, which is made of biocompatible material and has a device for fixing to a bone.

16 Claims, 6 Drawing Sheets

(51) Int. Cl.
*A61F 2/46* (2006.01)
*A61B 5/01* (2006.01)
*A61B 5/03* (2006.01)
*A61B 5/11* (2006.01)
*A61B 5/145* (2006.01)
*A61B 17/84* (2006.01)
*A61B 17/86* (2006.01)
*A61F 2/32* (2006.01)
*A61F 2/48* (2006.01)
*A61B 17/56* (2006.01)
*A61B 17/00* (2006.01)

(52) U.S. Cl.
CPC ............... *A61B 17/84* (2013.01); *A61B 17/86* (2013.01); *A61B 2017/00022* (2013.01); *A61F 2/32* (2013.01); *A61F 2002/4658* (2013.01); *A61F 2002/4668* (2013.01); *A61F 2002/4672* (2013.01); *A61F 2002/4674* (2013.01); *A61F 2002/488* (2013.01); *A61F 2250/0002* (2013.01)

(56) References Cited

U.S. PATENT DOCUMENTS

| | | |
|---|---|---|
| 8,095,198 B2 | 1/2012 | Nycz |
| 2006/0047283 A1* | 3/2006 | Evans, III ............... A61B 5/076 606/102 |
| 2006/0247773 A1* | 11/2006 | Stamp ................... A61B 5/076 623/17.11 |
| 2007/0179739 A1 | 8/2007 | Donofrio |
| 2009/0198155 A1 | 8/2009 | Bonnet |
| 2010/0100011 A1 | 4/2010 | Roche |
| 2011/0173831 A1 | 7/2011 | Caritu |
| 2012/0041713 A1 | 2/2012 | Bonnet |
| 2012/0072165 A1 | 3/2012 | Jallon |
| 2012/0078594 A1 | 3/2012 | Jallon |

FOREIGN PATENT DOCUMENTS

| | | |
|---|---|---|
| WO | 2006055547 A2 | 5/2006 |
| WO | 2009095768 A2 | 8/2009 |
| WO | 2010003824 A2 | 1/2010 |
| WO | 2010097422 A1 | 9/2010 |
| WO | 2010112469 A1 | 10/2010 |
| WO | 2010112470 A1 | 10/2010 |

* cited by examiner

DEVICE FOR MONITORING A MEDICAL PROSTHESIS AND THE HUMAN BODY

TECHNICAL FIELD OF THE INVENTION

The present invention relates to the field of prostheses, and relates more particularly to the field of so-called "intelligent" prostheses.

In order to monitor the behavior of a prosthesis implanted in the body of a patient, for example its osteo-integration or its wear, attempts have been made to include sensor means in the prosthesis, with wireless transmission means making it possible to transmit the data outside the body of the patient.

To this end, the document WO 2009/095768 is notably known.

The integration of sensor means in a prosthesis, however, demands a total redesign of conventional prostheses which hitherto were giving total satisfaction. It is, among other things, necessary to check that the integration of the sensor means does not compromise the mechanical strength of the prosthesis. This entails lengthy and costly studies for requalifying the prosthesis with the competent organizations.

Furthermore, it is not always possible to integrate sensor means in the existing prostheses, because of their shape or their section.

Another drawback is that, should the sensor means fail, it is necessary to remove the implanted prosthesis even though the latter may be functioning perfectly well. The removal of a prosthesis often causes additional damage, which generally results in the consequential implantation of a so-called "return" prosthesis which is more often than not more bulky and less effective.

Another drawback is that the patient has to decide before the fitting of the prosthesis whether or not he accepts, definitively, monitoring by sensor means.

Another drawback is that, if the patient decides, or is constrained, after the fitting of the prosthesis, to accept monitoring by sensor means, it is then necessary to remove the implanted prosthesis to replace it with a prosthesis with sensor means. This prosthesis with sensor means is then of the return prosthesis type.

Another drawback is that, if an unpredicted pathology occurs, it is possible that the sensor means present in the implanted prosthesis are unsuitable for monitoring the latter. It is therefore necessary to be able to choose and adapt the sensor means used according to a foreseeable or declared pathology, and do so after the prosthesis has been implanted.

To that is added a cost drawback, a prosthesis equipped with sensor means being very expensive.

Another drawback is that the sensor means are generally powered by a battery which has a limited life span and that has to be able to be changed regularly. Also repeated maintenance and/or replacements of the sensor means may entail their complete removal and reimplantation. The bone mass to which the prosthesis and/or the sensor means is fixed is thus repeatedly degraded or embrittled. Such is notably the case in the documents US 2007/0179739, US 2007/0179568, US 2010/0100011 and WO 2006/055547.

SUMMARY OF THE INVENTION

A first aim of the invention is to allow for a monitoring of a prosthesis by sensor means regardless of the shape or the configuration of the prosthesis.

Another aim of the invention is to enable the patient to make a reversible choice as to the monitoring or non-monitoring of the prosthesis, that does not effect the prosthesis-fitting operation to be performed or that has been performed.

Another aim of the invention is to allow for maintenance and/or replacement operations while limiting the degradation and the embrittlement of the surrounding bone mass.

To achieve these aims, and others, the invention proposes a device for monitoring a medical prosthesis and the human body, comprising:

sensor means, capable of generating signals according to surrounding stresses, processing means, capable of processing the signals transmitted by the sensor means to convert them into data, storage means, capable of storing the data, means for wirelessly transmitting the stored data, electrical energy power supply means, in which said sensor, processing, storage, transmission and power supply means are included in at least one housing made of biocompatible material, and in which said at least one housing is secured reversibly to fixing means by locking means, said fixing means being intended and designed to be fixed to a bone.

Such a device makes it possible to resolve the abovementioned drawbacks.

In particular, the sensor means are completely independent of the prosthesis to be monitored, while being able to be placed in immediately proximity thereto in order to monitor it effectively. The prostheses that are known and recognized for their good operation can be used normally, without requiring modification or requalification.

The installation of the sensor means can be performed during or after the implantation of the prosthesis.

An intervention on the sensor means has no impact on the implanted prosthesis.

The removal of the housing for its replacement or its maintenance is performed simply by means of the reversible locking means. The fixing means remain permanently in place in the bone mass and can thus be osteo-integrated satisfactorily.

Advantageously, the monitoring device comprises at least one first housing, containing the electrical energy power supply means, and which is linked to a second housing by electrical conduction means.

The electrical energy source, which is generally the most bulky element when the aim is to have significant durability in time, can be placed at a distance from the prosthesis, at a place and in an arrangement which do not provide any inconvenience. On the other hand, the sensor means will be able to be contained in the second housing which will then be able to have a small footprint in order to be placed in the immediate vicinity of the prosthesis in order to better monitor the latter.

Preferably, provision can be made for:

the device to comprise at least one first housing and one second housing, at least one of the two housings to comprise sensor means designed to detect the relative position of the other housing.

By fixing the housings to two bones situated on either side of a prosthetic articulation, it is thus possible to record the movements of the articulation in terms of number of cycles and/or in terms of amplitude, as is for example explained in the document WO 2010/003824. Data is then available for assessing the stress of the prosthesis, the quality of operation of the prosthesis and/or its remaining operational time span.

Advantageously, provision can be made for:

the device to comprise at least one first housing and one second housing, the device to comprise means for communication between the first and second housings, enabling one and/or the other of the housings to receive data from the other housing, at least one of the housings to comprise means for wirelessly transmitting the stored data to transmit the data received from the other housing.

Preferably, the sensor means can be sensitive to electrical, chemical, mechanical or optical stresses.

Among the mechanical sensors, the following can be used, depending on the data that is to be obtained: a gyrometer, an inclinometer (preferably of magnetometer type), or even an accelerometer.

It will also be possible to provide a pressure sensor, designed to assess the pressure in the medium surrounding the prosthesis.

Advantageously, the sensor means may comprise a sensor for measuring the conductivity of the surrounding medium. Such a sensor will notably make it possible to detect premature wear of a metallic prosthesis, this wear resulting in the release and dispersion of metal particles into the human body in the vicinity of the prosthesis.

A temperature sensor can be used in order to identify the presence of any infection, inflammation or other reaction with thermal manifestation in the body in the vicinity of the prosthesis.

Preferably, the sensor means may comprise a sensor for measuring pH.

Advantageously, the sensor means may comprise an optical sensor designed to detect the color of the surrounding medium. The detection of a change of color may manifest a physical-chemical reaction that is the sign of a malfunction, of an infection or of a pathology.

Preferably, electrical energy power supply means may comprise:

means for converting accelerations undergone by said at least one housing to convert them into electrical energy, means for storing the converted electrical energy.

There is thus a renewable energy source which is available when it is important to perform measurements and/or detections of movements.

Advantageously, provision can be made for:

the device to comprise means for disabling some sensor means and/or processing means, the disabling means are configured to disable the operation of these sensor means and/or processing means during predetermined time bands.

The disabling means make it possible to save energy, and thus increase the lifetime of the device in the case of a non-renewable energy source of battery type for example.

Preferably, provision can be made for:

the device to comprise means for disabling some sensor means and/or processing means, the disabling means to be configured to allow the operation of the processing means only after the non-disabled sensor means have detected movements for a duration greater than a predetermined duration.

This means that only movements of an amplitude greater than a predetermined amplitude will be detected, without movements occurring for sequences that are too short to have an impact on the life span and operation of the prosthesis being taken into account.

Again, for the purpose of not unnecessarily using energy for the monitoring and analysis of insignificant movements or movements with little meaningful influence, provision can be made for:

the device to comprise means for disabling some sensor means and/or processing means, the disabling means to be configured to allow the operation of the processing means only after the non-disabled sensor means have detected movements with an amplitude greater than a predetermined amplitude.

Advantageously, provision can be made for:

the data storage means to contain predetermined reference data, the device to comprise comparison means, designed to compare the data obtained from the processing of the signals transmitted by the sensor means with the predetermined reference data, in the event of nonconformity of the data obtained from the processing of the signals transmitted by the sensor means with the predetermined reference data, an anomaly signal to be generated and stored in the storage means.

By scanning the anomaly signals stored in the storage means, it is thus possible to continuously monitor the conformity of the operation of the prosthesis or of its surrounding medium with predetermined reference data corresponding to normal operation or to a normal surrounding medium. Any deviation with respect to a normal situation is thus detected.

To ensure the most intimate link possible with the bone on which the device is fixed, said at least one housing may comprise a face intended to bear against the bone by means of a shaping adapted to the external shape of the bone.

Alternatively, in order to have a housing of unique form that can be adapted to any bone, provision can be made for the device to comprise a shim comprising:

a first face intended to bear against the bone by means of a shaping adapted to the external shape of the bone, a second face, substantially opposite the first face, intended to bear against a face of said at least one housing by means of a shaping adapted to the face of said at least one housing.

Advantageously, the fixing means of said at least one housing may comprise:

a single screw for securing said at least one housing to the bone, means for blocking the rotation of said at least one housing relative to the securing screw or relative to the bone.

A single securing screw makes it possible to affect the bone as little as possible while the rotation blocking means ensure a constant orientation of the housing, notably for the movement detection and analysis to be performed in constant directions.

Preferably, provision can be made for:

the fixing means to comprise at least one securing screw or, if appropriate, a single securing screw, the securing screw to comprise a bottom part with thread with osteo-integration means, the securing screw to comprise a top part designed to cooperate with the locking means of said at least one housing on the top part in order to retain said at least one housing.

The securing screw is thus permanently fixed in the bone for a perfect retention of the housing which will still, despite everything, be able to be dismantled and reassembled for maintenance or replacement needs, without affecting the surrounding bone mass.

Preferably, provision can be made for:

said at least one housing to be a hollow tubular housing, extending in a longitudinal direction, capable of being locked in a substantially tubular sleeve with outer wall provided with an outer threading, the tubular housing and/or the substantially tubular sleeve to comprise an end provided with means for driving in rotation about the longitudinal direction.

The housing thus substantially takes the form of a screw that can be directly implanted by screwing into the bone of the patient. Once implanted, the housing can protrude little from the bone, to limit the risk of conflict with the surrounding tissues and flesh.

BRIEF DESCRIPTION OF THE DRAWINGS

Other objects, features and advantages of the present invention will emerge from the following description of particular embodiments, given in relation to the appended figures, in which.

DESCRIPTION OF PREFERRED EMBODIMENTS

Figure 1:
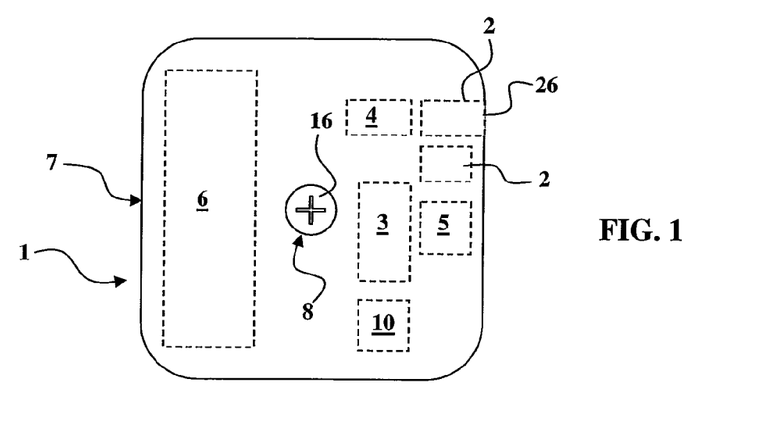
FIG. 1 is a plan view of a device for monitoring a medical prosthesis and the human body, according to a first embodiment of the invention.
Figure 6:
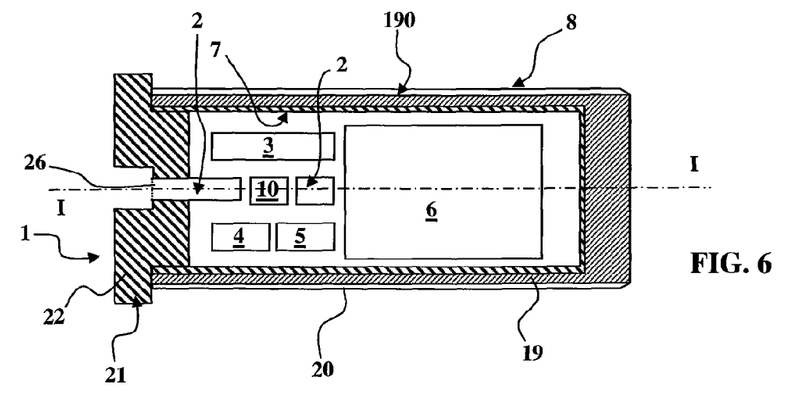
FIG. 6 is a schematic cross-sectional side view of a device for monitoring a medical prosthesis and the human body, according to a third embodiment of the invention.

FIGS. 1 and 6 respectively illustrate two embodiments of the device for monitoring a medical prosthesis and the human body. In each of these figures, a device 1 for monitoring a medical prosthesis and the human body can be distinguished, comprising:

sensor means 2, capable of generating signals according to surrounding stresses, processing means 3, capable of processing the signals transmitted by the sensor means 2 to convert them into data, storage means 4, capable of storing the data, means 5 for wirelessly transmitting the stored data, electrical energy power supply means 6, a leak-tight housing 7 made of biocompatible material, in which are included the sensor 2, processing 3, storage 4, transmission 5 and power supply 6 means, the housing 7 comprising means 8 for fixing to a bone.

Control means (not represented) drive one or more of the sensor means 2, of the processing means 3, of the storage means 4, of the transmission means 5 and of the power supply means 6.

Examples of biocompatible materials from which to make the leak-tight housing 7 are: titanium, titanium alloy, stainless steel, polymer (notably PEEK).

In a variant not represented in the figures, the device 1 comprises at least one first housing, containing the electrical energy power supply means 6, and which is linked to a second housing by electrical conduction means.

Figure 9:
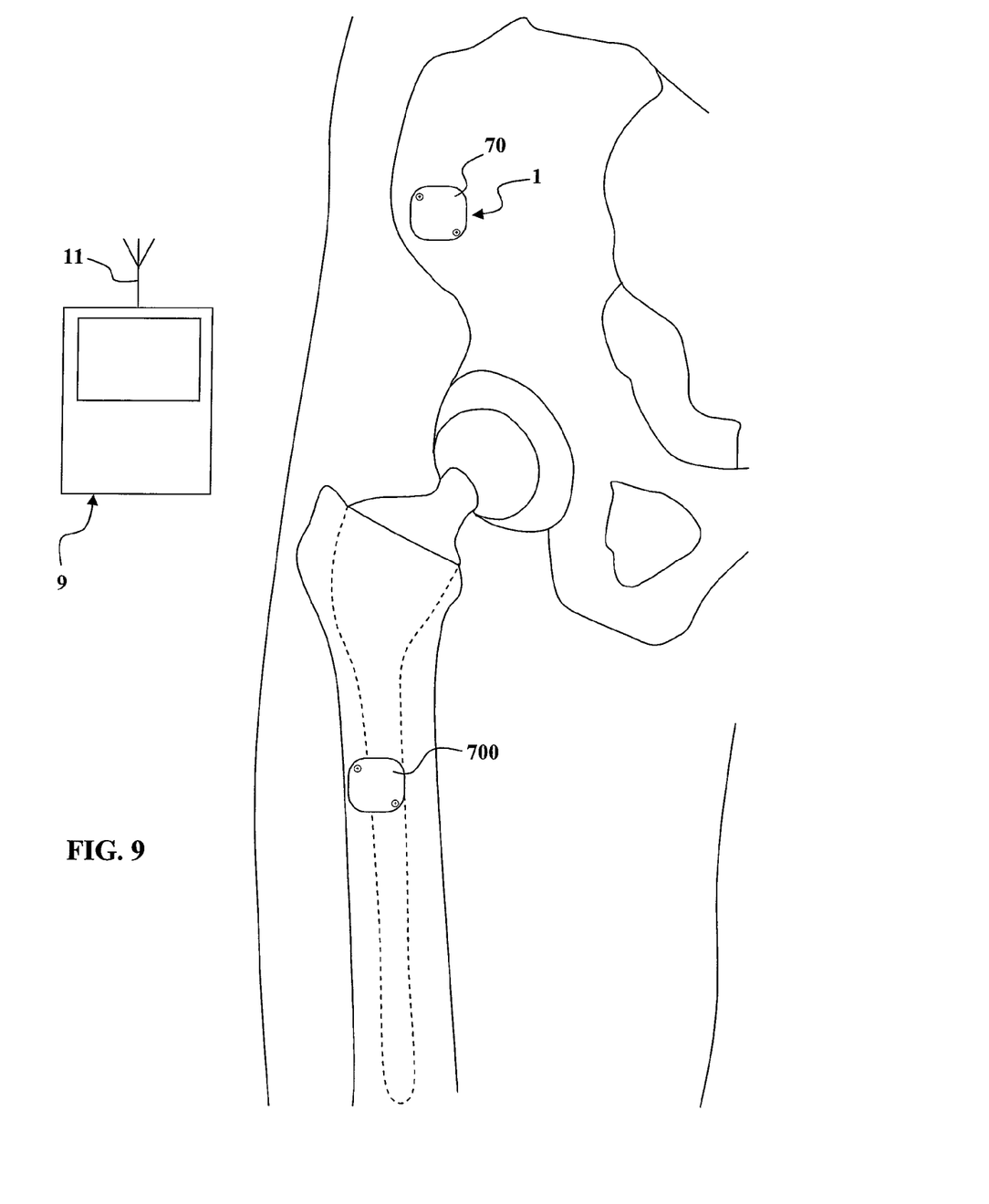
FIG. 9 is a schematic view illustrating an example of operation of a device for monitoring a medical prosthesis and the human body according to the invention.

In the variant illustrated in FIG. 9, the device 1 comprises:

a first housing 70 and a second housing 700, at least one of the two housings 70 or 700 comprises sensor means 2 (not visible) designed to detect the relative position of the other housing.

For such sensor means 2, reference can notably be made to the teachings of the document WO 2010/003824.

In order to make use of the stored data, the latter are transmitted to a remote terminal 9 provided with reception means 11. The remote terminal 9 and the reception means 11 are designed to directly receive the data stored in the first housing 70 via the transmission means of the housing 70 and to directly receive the data stored in the second housing 700 via the transmission means of the second housing 700.

It is, however, possible for a direct transmission between the first housing 70 or the second housing 700 and the remote terminal 9 to be subject to a wave propagation defect. For example, fatty tissues may absorb a significant proportion of the waves and thus prevent the transmission of the stored data directly from one of the housings 70 or 700 to the remote terminal 9. In this case, it is advantageous to provide for:

the device 1 to comprise means for communication between the first and second housings 70 and 700, enabling one and/or the other of the housings 70 or 700 to receive data from the other housing 70 or 700, at least one of the housings 70 or 700 to comprise means for wirelessly transmitting the stored data in order to transmit the data received from the other housing 70 or 700.

The first housing 70 and/or the second housing 700 can thus act as a relay in the transmission of the stored data contained in the other of the housings 70 or 700.

Figure 2:
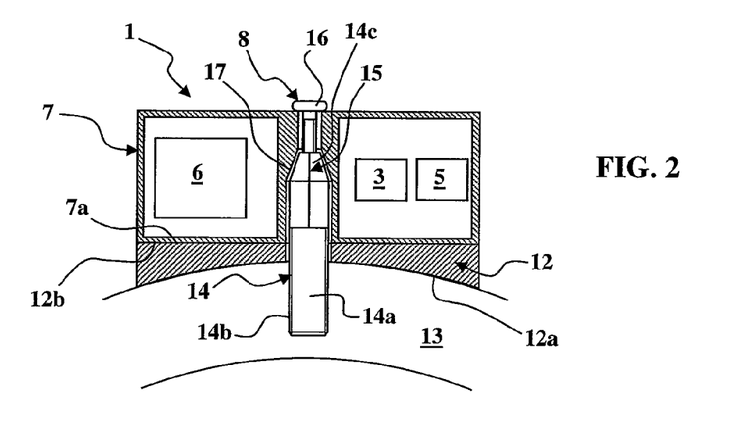
FIGS. 2 and 3 are schematic cross-sectional front views of two variants of the device of FIG. 1.

FIG. 2 illustrates a variant of a device of FIG. 1 comprising a shim 12 which comprises:

a first face 12a intended to bear against the bone 13 by means of a shaping adapted to the external shape of the bone 13, a second face 12b, substantially opposite the first face 12a, intended to bear against a face 7a of the housing 7 by means of a shaping adapted to the face 7a of the housing 7.

The housing 7 thus comes indirectly into intimate contact with the bone 13.

Figure 3:
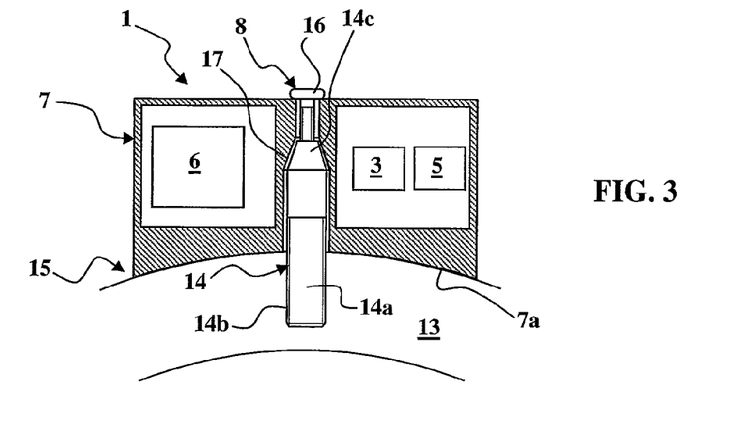

In another variant illustrated in FIG. 3, the housing 7 can itself comprise a face 7a intended to bear against the bone 13 by means of a shaping adapted to the external shape of the bone 13.

The variant of FIG. 2 offers the advantage, compared to the variant of FIG. 3, of having to change only the shim 12 according to the shape of the bone, in order to fix a unique housing 7 of standardized shape.

FIG. 2 shows that the fixing means 8 of the housing 7 comprise:

a single screw 14 for securing the housing 7 to the bone 13, means for blocking the rotation 15 of the housing 7 relative to the securing screw 14.

For this, provision is made for:

the securing screw 14 to comprise a bottom part 14a with thread 14b with osteo-integration means, the securing screw 14 to comprise a top part 14c comprising locking means 16 for the housing 7 on the top part 14c.

In practice, it can be seen in FIG. 2 that the top part 14c of the securing screw 14 has a non-circular section to cooperate, by complementarity of shapes, with a recess 17 providing in the housing 7 to receive the top part 14c.

Alternatively, as represented in FIG. 3, the fixing means 8 of the housing 7 may comprise:

a single screw 14 for securing the housing 7 to the bone 13, means for blocking the rotation 15 of the housing 7 relative to the bone 13.

In FIG. 3, the rotation blocking means 15 consist of the face 7a of the housing 7 bearing against the bone 13. There is therefore no need, in this case, for the top part 14c of the securing screw 14 to cooperate by complementarity of shapes with the recess 17 of the housing 7 intended to receive the top part 14c.

It should be noted that, in the case of FIGS. 2 and 3, the securing screw 14 is permanently fixed into the bone 13 but the housing 7 can freely be removed for a replacement or maintenance operation. The dismantling of the housing 7 is performed by unscrewing the locking means 16 which are reversible and which take the form of a screw screwed into the top part 14c of the securing screw 14. The dismantling of the housing 7 for its replacement or maintenance therefore does not affect the bone mass of the patient which will grow and consolidate without disruption around the securing screw 14.

Figure 4:
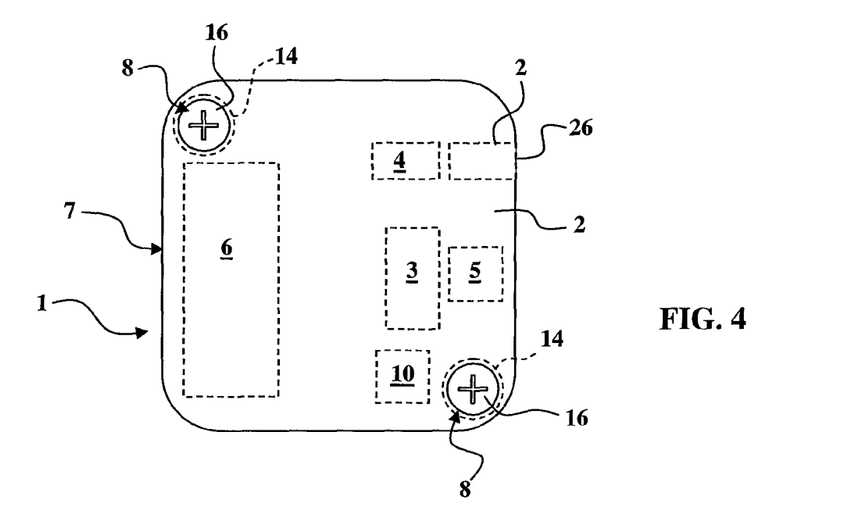
FIG. 4 is a plan view of a variant of the device of FIG. 1.

In a variant illustrated in FIG. 4, the housing 7 is fixed to a bone via fixing means 8 comprising two securing screws 14, the top parts 14c of which do not have any rotation blocking means that block the rotation of the housing relative to the bone. These two securing screws 14 simultaneously make it possible to securely attach the housing 7 to the bone and ensure a constant orientation of the housing 7 relative to the bone on which it is fixed.

Depending on the thickness of the bone mass and the state of this bone mass, it may be possible to make use of screw-fixing means 8. In this case, use is made of a device 1 illustrated in FIG. 5 (which does not form part of the present invention), which comprises a housing 7 in the form of a peanut or a figure "8" and fixed to the bone 13 via a flexible link 18 gripping the bone 13.

Figure 5:
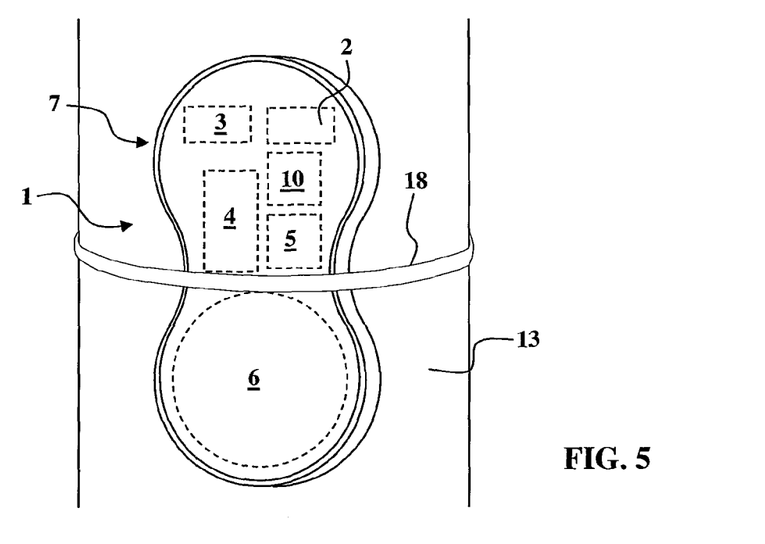
FIG. 5 is a perspective view of a device for monitoring a medical prosthesis and the human body that does not form part of the present invention.

The flexible link 18 and the shape of the housing cooperate to ensure a constant orientation of the housing 7 relative to the bone 13. It should be noted that other outer shapes of the housing 7 could be used in cooperation with the flexible link 18 to guarantee a constant orientation of the housing 7 relative to the bone 13.

Figure 7:
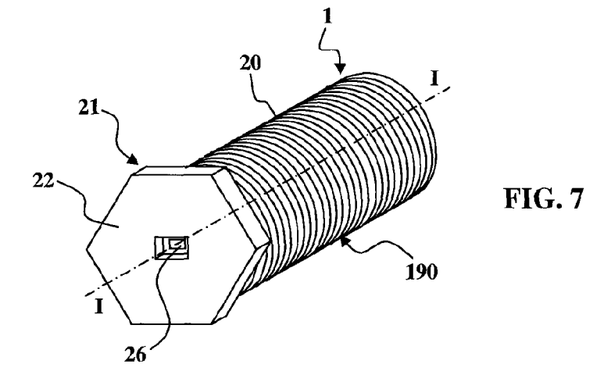
FIG. 7 is a perspective view of the device of FIG. 6.

A third embodiment of the invention is illustrated in FIGS. 6 and 7.

In these figures, it can be seen that:

the housing 7 is a hollow tubular housing extending in a longitudinal direction II, capable of being locked in a substantially tubular sleeve 190 with outer wall 19 provided with an outer threading 20, the tubular housing comprises an end 21 provided with means for driving in rotation 22 about the longitudinal direction II.

In the case in point, the rotation driving means 22 comprise a hexagonal head that makes it possible to screw the housing 7 into the bone mass of the patient.

Figure 8:
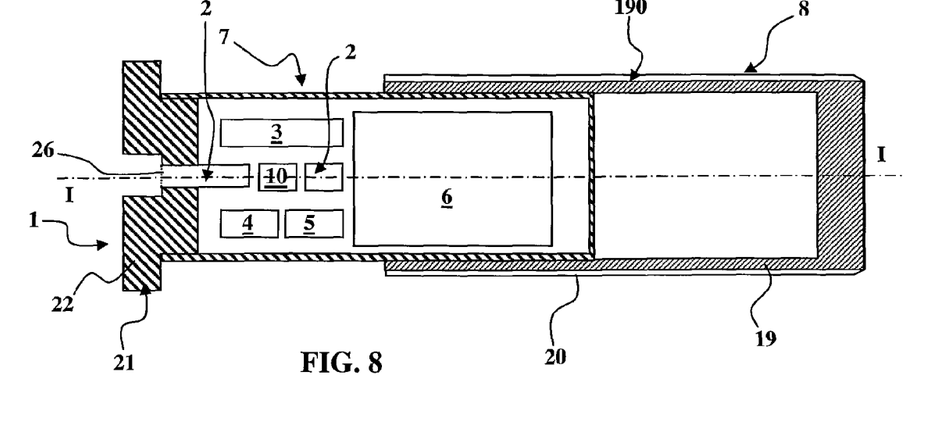
FIG. 8 is a schematic cross-sectional side view of a variant of the device of FIG. 6.

It can be seen more particularly in FIG. 8 that the fixing means 8 comprise the substantially tubular sleeve 190 with outer wall 19 provided with an outer threading 20. The housing 7 is fitted into the tubular sleeve 190 by force-fitting and/or by complementarity of shapes (screwing or snap-fitting for example), or by any other suitable reversible locking means, so that the driving in rotation in the longitudinal direction II of the housing 7 via the rotation driving means 22 simultaneously drives in rotation the outer wall 19 so as to penetrate by screwing into a bone mass.

It is thus possible to remove the housing 7 and its content in order to perform a maintenance or replacement operation thereon without having to extract the threaded outer wall 19 which can remain permanently in place in the bone mass of the patient, which will not therefore be degraded by the maintenance or replacement operation.

Figure 11:
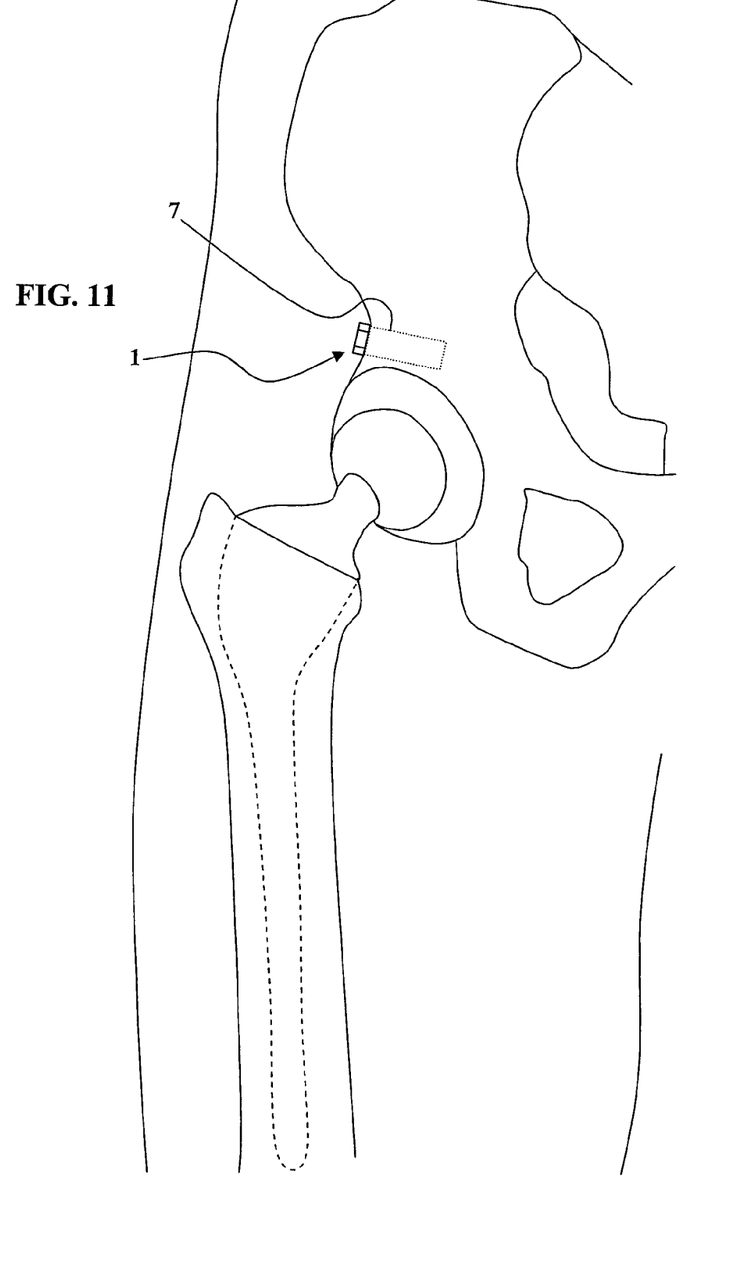

In the variant illustrated in FIGS. 6 to 8, the device 1 according to the invention takes the outer form of a screw. This screw will be able to be implanted for example in the pelvis of the patient as represented in FIG. 11.

Figure 10:
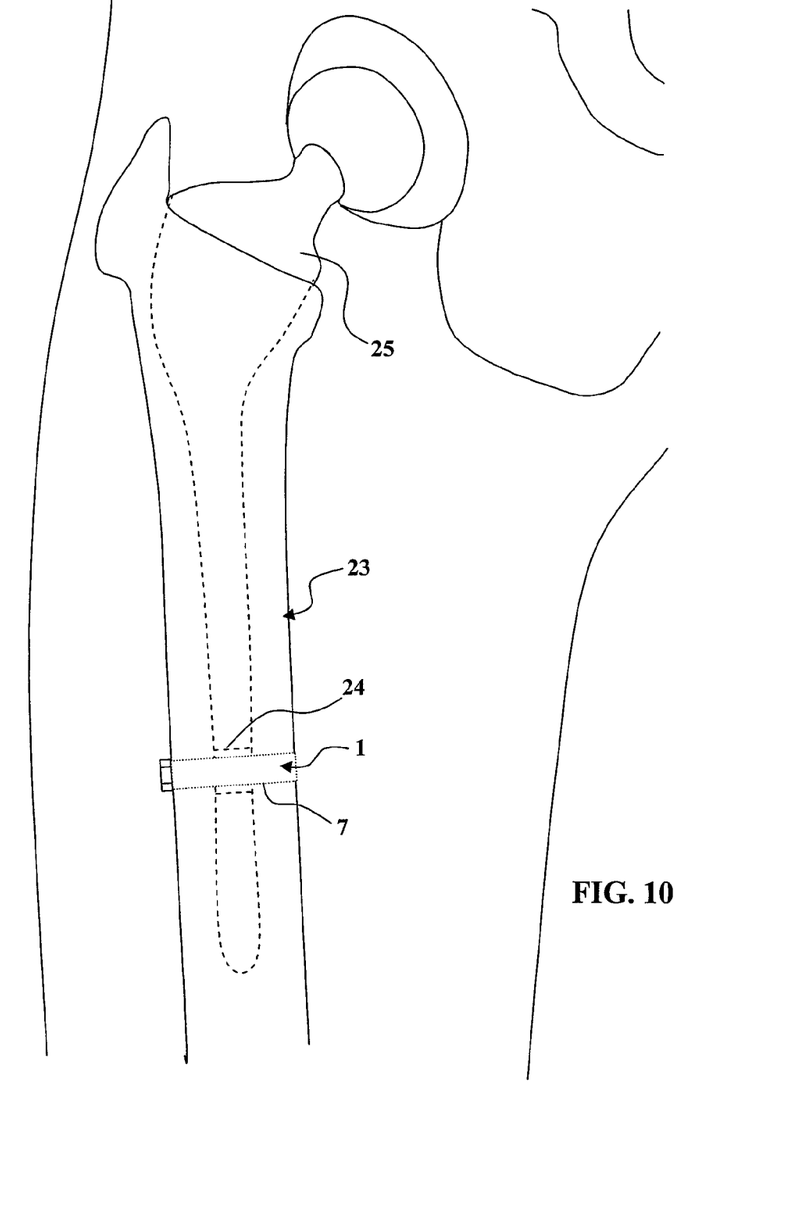
FIGS. 10 and 11 are schematic views illustrating examples of implantation of the device of FIGS. 6 to 8.

The device 1 of FIGS. 6 to 8 will, however, also be able to fulfill the functions of locking screw as illustrated in FIG. 10 where the threaded housing 7 is screwed into the femur 23 of the patient by passing through an opening 24 provided in a femoral rod 25 of the hip prosthesis. The housing 7 with outer threading thus fulfills a function of axial locking of the femoral rod 25. Such an implantation in the femur 23 is also possible but without ensuring any axial locking of a femoral rod.

In all the embodiments described previously, the sensor means 2 may be sensitive to electrical, chemical, mechanical or optical stresses.

In the case of sensor means 2 that need to perform measurements in the surrounding medium, such as a sensor of conductivity, of temperature, or of pH, it will be possible to make provision for said sensor means 2 to be located in immediate proximity to a wall of the housing 7, said sensor means 2 being in contact with the surrounding medium via a permeable wall portion 26 (FIGS. 1 and 4).

In FIGS. 1, 4, 5, 6 and 8, the device 1 comprises disabling means 10 for selectively disabling the sensor means 2 and/or the processing means 3.

In a first mode of operation, the disabling means are configured to disable the operation of the sensor means 2 and/or of the processing means 3 in predetermined time bands. For example, the disabling means 10 can disable the operation of the sensor means 2 and/or of the processing means 3 during the hours of the night for people generally inactive at night.

As an alternative, or in complement, the disabling means 10 are configured to allow the operation of the processing means 3 only after the sensor means 2 have detected movements for a duration greater than a predetermined duration.

Such a mode of operation makes it possible to effectively limit the quantity of signals transmitted by the sensor means 2 to be processed by the processing means 3. Such a mode of operation also makes it possible to limit the data stored by excluding a significant quantity of movements of short duration which are unlikely to generate a significant wear of the prosthesis. Also, this limiting of data simplifies and makes more reliable a statistical analysis of the data to draw clinical teachings therefrom.

As an alternative, or in complement, the disabling means 10 are configured to allow the operation of the processing means 3 only after the sensor means 2 have detected movements with an amplitude greater than a predetermined amplitude.

The use of the disabling means 10 described previously makes it possible to limit the quantity of data to be processed, to save electrical energy in order to increase the life of the device 1 while making it possible to increase the reliability of the statistical data which will be able to be established on the basis of the data stored then transmitted.

In order to refine the clinical tracking of the patients and better understand any malfunctions of the prosthesis, provision is made for:

the data storage means 4 to contain predetermined reference data, the device 1 to comprise comparison means, designed to compare the data obtained from the processing of the signals transmitted by the sensor means 2 with the predetermined reference data, in the event of nonconformity of the data obtained from the processing of the signals transmitted by the sensor means 2 with the predetermined reference data, an anomaly signal to be generated and stored in the storage means 4.

The predetermined reference data will, for example, be able to consist of movement amplitudes, movement angles or even movement execution angular velocities. It will thus be possible to monitor, over time, whether the prosthesis initially provided and implanted is still suited to the lifestyle and the behavior of the patient. It will also be possible to continuously check the conformity of the operation of the prosthesis or of its surrounding medium to detect any deviation relative to a situation that is estimated to be normal corresponding to the predetermined reference data.

It is expressly specified that the different sensor means 2, the electrical energy power supply means, the various energy-saving means, but also the different data processing methods by comparison with reference data form distinct inventions of the fixing and locking means and will be able to be the subject of independent protection.

To produce the sensor means 2 and the processing means 3, reference will be able to be made to the teachings of the documents EP 2 106 747, WO 2010/097422, WO 2010/112469 and WO 2010/112470.

The present invention is not limited to the embodiments which have been explicitly described, but it includes the various variants and generalizations thereof contained within the scope of the claims below.

The invention claimed is:

1. A device for monitoring a medical prosthesis and the human body, comprising:
    a sensor, capable of generating signals according to surrounding stresses,
    a processor, capable of processing the signals transmitted by the sensor to convert them into data,
    a storage device, capable of storing the data,
    a wireless transmitter for wirelessly transmitting the stored data,
    an electrical energy power supply,
    in which said sensor, processor, storage device, transmitter and power supply are included in at least one housing made of biocompatible material,
    wherein said at least one housing is a hollow tubular housing, extending in a longitudinal direction (I-I) and is secured reversibly to a substantially tubular sleeve with outer wall provided with an outer threading, said substantially tubular sleeve being intended and designed to be fixed to a bone,
    wherein:
    the tubular housing and/or substantially tubular sleeve comprises an end provided with means for driving in rotation about the longitudinal direction (I-I).

2. The device as claimed in claim 1, wherein the sensor is sensitive to electrical, chemical, mechanical or optical stresses.

3. The device as claimed in claim 1, wherein the sensor comprises a gyrometer.

4. The device as claimed in claim 1, wherein the sensor comprises an inclinometer.

5. The device as claimed in claim 4, wherein said inclinometer is of magnetometer type.

6. The device as claimed in claim 1, wherein the sensor comprises an accelerometer.

7. The device as claimed in claim 1, wherein the sensor comprises a pressure sensor.

8. The device as claimed in claim 1, wherein the sensor comprises a sensor for measuring the conductivity of the surrounding medium.

9. The device as claimed in claim 1, wherein the sensor comprises a temperature sensor.

10. The device as claimed in claim 1, wherein the sensor comprises a sensor for measuring the pH.

11. The device as claimed in claim 1, wherein the sensor comprises an optical sensor designed to detect the color of the surrounding medium.

12. The device as claimed in claim 1, wherein the electrical energy power supply comprises a renewable energy source configured to convert
    accelerations undergone by said at least one housing into electrical energy.

13. The device as claimed in claim 1, further comprising a controller
    to disable the operation of the sensor and/or processor during predetermined time bands.

14. The device as claimed in claim 1, further comprising a controller
    to allow the operation of the processor only after the sensor has detected movements for a duration greater than a predetermined duration.

15. The device as claimed in claim 1, further comprising a controller
    to allow the operation of the processor only after the sensor has detected movements with an amplitude greater than a predetermined amplitude.

16. The device as claimed in claim 1, wherein:
    the storage device contains predetermined reference data,
    the device comprises comparison means, designed to compare the data obtained from the processing of the signals transmitted by the sensor with the predetermined reference data,
    in the event of nonconformity of the data obtained from the processing of the signals transmitted by the sensor with the predetermined reference data, an anomaly signal is generated and stored in the storage device.

* * * * *

UNITED STATES PATENT AND TRADEMARK OFFICE
CERTIFICATE OF CORRECTION

PATENT NO.        : 9,629,583 B2
APPLICATION NO.   : 14/003293
DATED             : April 25, 2017
INVENTOR(S)       : Thomas Gradel et al.

Page 1 of 1

It is certified that error appears in the above-identified patent and that said Letters Patent is hereby corrected as shown below:

On the Title Page

In the listing of inventors, regarding inventor Fabien Gaucher, delete "Lyons" and insert instead --Lyon--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*